(12) United States Patent
Leeungculsatien (10) Patent No.: US 12,372,389 B2
(45) Date of Patent: Jul. 29, 2025

(54) FLOW METER FOR MEASURING FLOW VELOCITY IN OIL CONTINUOUS FLOWS

(71) Applicant: Roxar Flow Measurement AS, Stavanger (NO)

(72) Inventor: Teerachai Leeungculsatien, Sandnes (NO)

(73) Assignee: Roxar Flow Measurement AS, Stavanger (NO)

( * ) Notice: Subject to any disclaimer, the term of this patent is extended or adjusted under 35 U.S.C. 154(b) by 239 days.

(21) Appl. No.: 17/918,499

(22) PCT Filed: Jun. 11, 2021

(86) PCT No.: PCT/EP2021/065733
§ 371 (c)(1),
(2) Date: Oct. 12, 2022

(87) PCT Pub. No.: WO2021/250225
PCT Pub. Date: Dec. 16, 2021

(65) Prior Publication Data
US 2023/0142240 A1    May 11, 2023

(30) Foreign Application Priority Data
Jun. 12, 2020   (NO) .................................. 20200698

(51) Int. Cl.
*G01F 1/74*    (2006.01)
*G01F 1/56*    (2006.01)
(Continued)

(52) U.S. Cl.
CPC ................. *G01F 1/74* (2013.01); *G01F 1/56* (2013.01); *G01N 33/2847* (2013.01); *G01R 15/148* (2013.01)

(58) Field of Classification Search
CPC ... G01F 1/74; G01F 1/56; G01F 1/584; G01F 1/60; G01F 1/58; G01N 33/2847;
(Continued)

(56) References Cited

U.S. PATENT DOCUMENTS 5,421,210 A * 6/1995 Kobayashi .............. G01F 1/002
73/861.12
7,276,916 B2   10/2007 Hammer
(Continued)

FOREIGN PATENT DOCUMENTS

JP      2015227874 A    12/2015
WO   WO-2007009097 A1   1/2007
(Continued)

OTHER PUBLICATIONS

Myrillas, K.; International Search Report; PCT/EP2021/065733; Dated: Sep. 16, 2021; 4 pages.

*Primary Examiner* — Timothy P Graves
(74) *Attorney, Agent, or Firm* — Bradley Arant Boult Cummings LLP (57) ABSTRACT

Flow meter and method for measuring the flow velocity of an oil continuous multiphase flow, said flow including water droplets. The flow meter including at least one magnetic field generator configured to provide a magnetic field with a known strength into said flow, the flow meter also including at least one sensor for measuring the charge at the sensor relative to a ground level, the sensor being positioned at a distance from the center of the magnetic field axis and the flow axis, in essentially the same axial position as the magnetic field axis, wherein the meter also including a calculating means for calculating a measure of the flow velocity based on the measured charge.

11 Claims, 6 Drawing Sheets

(51) Int. Cl.
*G01N 33/28* (2006.01)
*G01R 15/14* (2006.01)

(58) Field of Classification Search
CPC ........ G01N 22/04; G01N 27/22; G01N 33/28; G01R 15/148
See application file for complete search history.

(56) References Cited

U.S. PATENT DOCUMENTS

| | | |
|---|---|---|
| 9,163,967 B2 | 10/2015 | Lucas et al. |
| 2005/0109120 A1* | 5/2005 | Turner .................... G01F 1/588 73/861.12 |
| 2012/0048030 A1 | 3/2012 | Furlong et al. |
| 2016/0076926 A1* | 3/2016 | McCann .................. G01F 1/60 73/861.04 |
| 2017/0261357 A1 | 9/2017 | Wang |

FOREIGN PATENT DOCUMENTS

| | | |
|---|---|---|
| WO | WO-2016042317 A1 | 3/2016 |
| WO | WO-2020084132 A1 | 4/2020 |

* cited by examiner

FLOW METER FOR MEASURING FLOW VELOCITY IN OIL CONTINUOUS FLOWS

The present invention relates to a flow meter and method for measuring the flow velocity of an oil continuous multiphase flow having a water content.

Measuring flow velocity and other parameters in multiphase fluid flows is important in hydrocarbon industry as well as other areas with complex flow content. Numerous solutions have been proposed and are in use, such as differential pressure in venturis or inserts, ultrasonic doppler measurements and electromagnetic measurements. Often flow measurements use a number of different sensors, electrodes and devices making the measuring units complicated and expensive. Therefore, there is a need for reducing the number of components, especially those in direct contact with the flow, and if possible use the same sensors for measuring different flow parameters.

Using electrodes and electrical fields for flow measurements is shown in WO2020084132/NO20181382 where different types of electrode configurations are used for measuring the composition of the flow, but the measured variations may also be used to measure the flow velocity. The latter does, however, require a certain degree of variation in the flow composition.

Another method for measuring flow velocity is discussed in U.S. Pat. No. 9,163,967 and WO2007/009097. This solution is useful in water continuous situations where the water flows through a magnetic field which provides a voltage difference in the direction perpendicular to the magnetic field and the flow direction using electrodes position along the circumference of the pipe. The solution is, however, not suitable for nonconductive flows and therefor of limited use in hydrocarbon related measurements. In WO2007/009097 this is solved by using electrodes in the flow direction measuring the velocity if the water content in the flow gets too low.

It is therefore an object of the present invention to provide an alternative way for measuring flow velocity in nonconductive fluid flows where the flow has a stable regime and composition, preferably using existing electrode configurations. This object is obtained as specified in the accompanying claims.

The present invention is thus based on the fact that even in a non-conductive flow any conductive or dipole molecules will be affected by the magnetic field, making a difference in electrical charge in any direction apart from parallel to the magnetic field, and will be at maximum when perpendicular to the magnetic field. This may be measured using electrodes positioned at a distance from the magnetic field axis, measuring the charge relative to the ground level using a low impedance circuitry.

The present invention will be described below with reference to the accompanying drawings illustrating the invention by way of examples.

FIG. 1$a,b$ illustrates the measurements according to the prior art, e.g. as presented in U.S. Pat. No. 9,163,967.

FIG. 2$a,b$ illustrates the measurements according to the present invention.

FIG. 3$a$-$e$ illustrates the effects of the magnetic field on the water droplets in the flow according to the invention.

Figure 1A:
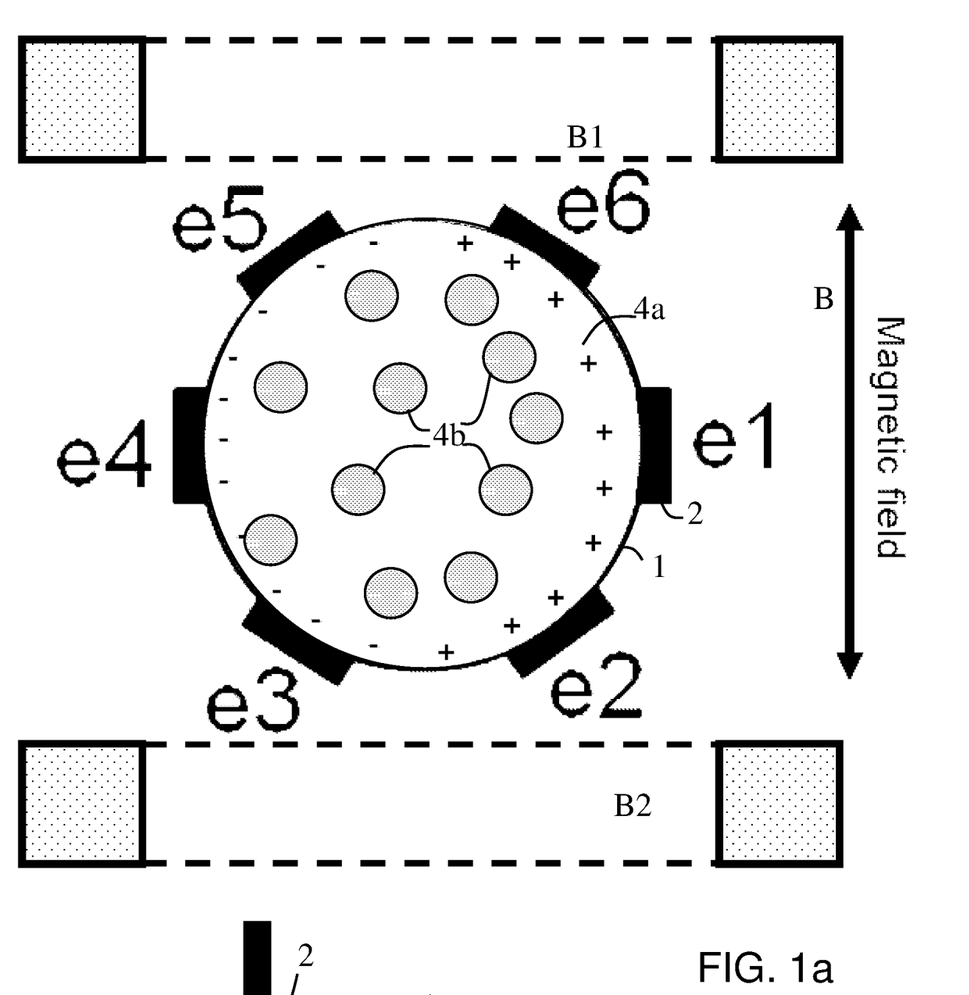

In the basic relation is of the known art is illustrated in FIG. 1$a$, illustrating the cross section of a pipe 1 with at least one electrode 2 used for measuring the velocity. Two coils B1,B2 are used to generate an essentially homogenous magnetic field B extending through the pipe 1, the pipe material being chosen so as not to disturb the magnetic field B. The measuring principle is based on the fact that as the water continuous fluid 4$a$, possibly including oil droplets 4$b$, flows through the magnetic field B Faradays law of induction states that an induced voltage is created when a moving conductor such as the water continuous flow passes through the magnetic field. This is indicated in FIG. 1$a$ as the positive and negative changes +/− at the pipe wall 1. The voltage induced by this can be measured at electrodes 2 positioned at a distance from the magnetic field axis and flow axis, the voltage thus corresponds to $$\Delta E = kBvD$$

$\Delta E$ is the potential between the two opposite electrodes, k is a calibration constant, B is magnetic field strength, v is the water velocity and D is the distant between the two-measuring electrode. The water velocity, v, can be simply calculated. It has been demonstrated, as discussed in U.S. Pat. No. 9,163,967, that a good performance may be achieved using the magnetic field and voltage measurements to measure water velocity in multiphase flow. The measured differential voltage is a function of local water velocity and local water volume fraction (WFV). Thus measured difference in potential is expressed as $$\Delta E = f(v_{ij}, wvf_{ij})$$

Figure 1B:
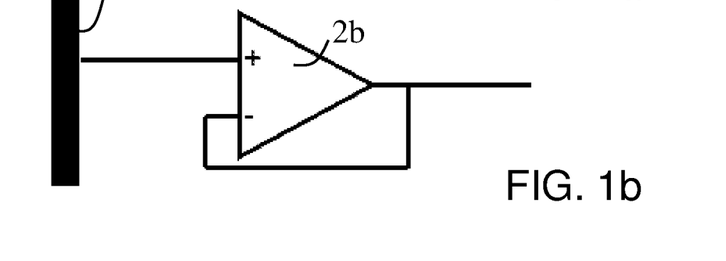

As can be seen in the lower part of FIG. 1$b$ the potential at the electrode 2 may be measured using well known circuitry 2$b$.

In FIG. 1$a$ the velocity electrode 2 is constituted by one of a number of electrodes e1-e6, e.g. used for permittivity measurements, which also can be used for velocity measurements at other positions relative to the magnetic field axis and thus also provide information about the velocity distribution over the pipe cross section.

Figure 2A:
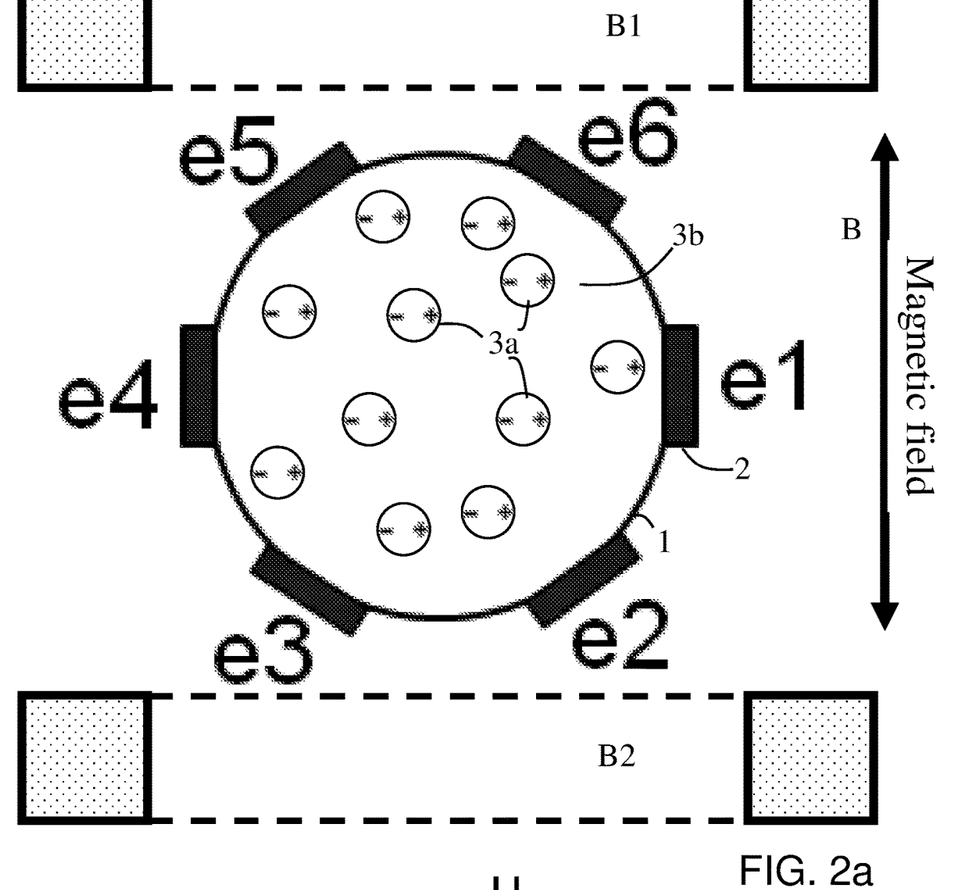
Figure 2B:
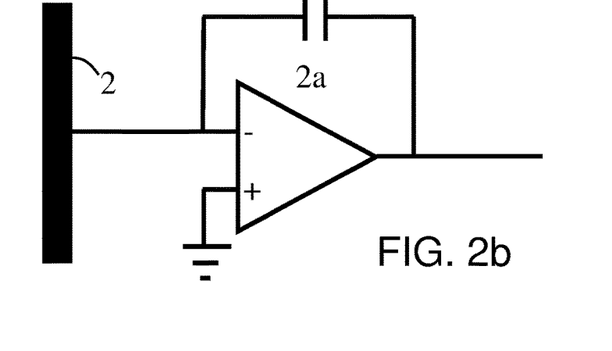

The present invention is illustrated in FIG. 2$a,b$, where magnetic field B is applied by to coil B1,B2 to provide an homogenous magnetic field B with a defined direction through a pipe 1 with an oil-continuous multiphase flow 3$b$ containing droplets of water 3$a$. The necessary amount of water will depend on the flow conditions and the accuracy of the measurements, but with a stable water content the relative differences in the measurements will provide an indication of the flow velocity of the fluid.

In addition to the Faradays law the droplets 3$a$ in the oil continuous flow 3$b$ the Lorentz force will apply combining the electric and magnetic force on the electrical charge in the water droplets 3$a$ in the hydrocarbon flow 3$b$. The electromagnetic field and the induced voltage gives an electromotive force that is defined by the circulation motion of the electrical charge in a conductor in the closed loop defined by the water droplet in the non-conducting flow. In FIG. 2$a$ this is illustrates by positive and negative charges in the droplets but in reality there is a circulation of charge in the droplets. The principles of this will be described more in detail below.

When the water droplet pass 3$a$ thought a magnetic field B, an induced electrical potential by the magnetic field is created within each water droplet 3$a$ as shown in FIG. 2$a$. These individual potentials will generate an electrical field which is capacitively coupled to an electrode, and the charge is pickup by the charge measurement electronic (charge amplifier) A. The measured differential charge is a function of local water velocity and local water volume fraction (WVF). However, measured differential charge has a linear relationship with water velocity but nonlinear relationship with WVF.

$$\Delta Q = f(v_{ij}, wvf_{ij})$$

where, $\Delta Q$ is the induced charge relative to ground.

This way a measured change in the charge will indicate a corresponding change in the flow velocity. The measurement may be relative, depending on change relative to a measurement under known conditions or be based on a predetermined model taking into account predetermined WVF measurements or WVF measured real-time in relation to the velocity measurement.

Again, in FIG. 2b the circuitry 2a for measuring the charge at each electrode is shown. The flow velocity can be measured using one electrode 2, preferably positioned in a position perpendicular to the magnetic field direction and flow direction to optimize the signal/noise ratio, but a number of electrodes e1-e6 may be used to provide an indication of the flow profile.

The magnetic field may be constant or varying at a known frequency. The latter would mean that the measured charge would change in synchronization with the varying field, which could be used to remove errors and disturbances in the measurements.

The measurements may be calibrated or adjusted for the known water volume fraction, salinity etc to reduce the uncertainty in the velocity measurements, either based on periodical samples of the flow content or by measurements performed in the vicinity of the measurements so as to have a precise knowledge about the flow conditions.

Figure 3A:
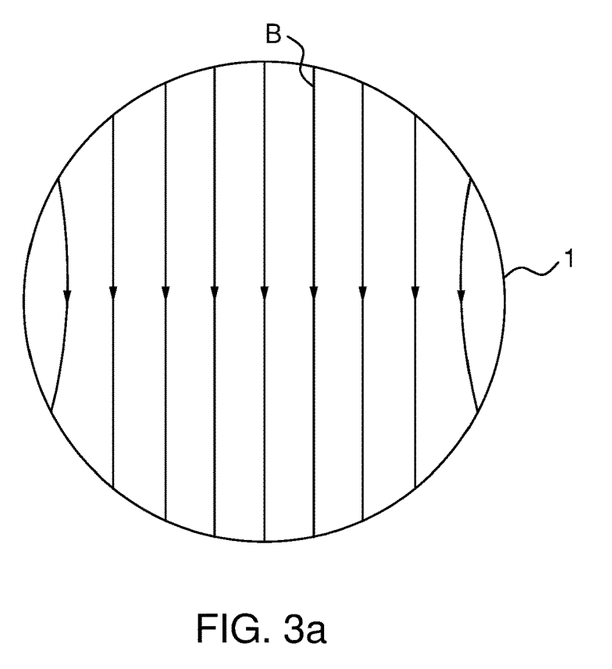

In FIGS. 3a-3e the principles behind the present invention is illustrated. In FIG. 3a the typical magnetic field B distribution in the pipe 1 is illustrated. This may deviate from the practical solutions depending on the coils and materials, possibly at a cost of less accurate measurements.

Figure 3B:
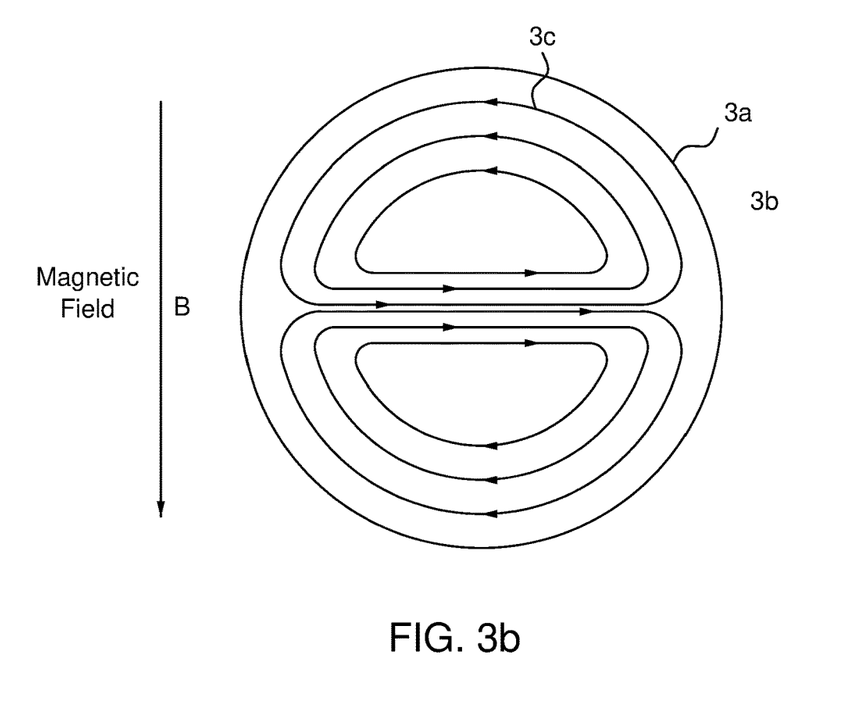

FIG. 3b shows the induced electrical current density 3c in a water droplet 3a traveling at a velocity under an imposed magnetic field B. The water droplet 3a is immersed in a non-conducting phase (gas or oil) multiphase flow 3b. Note that the denser lines represent increasing current density.

Figure 3C:
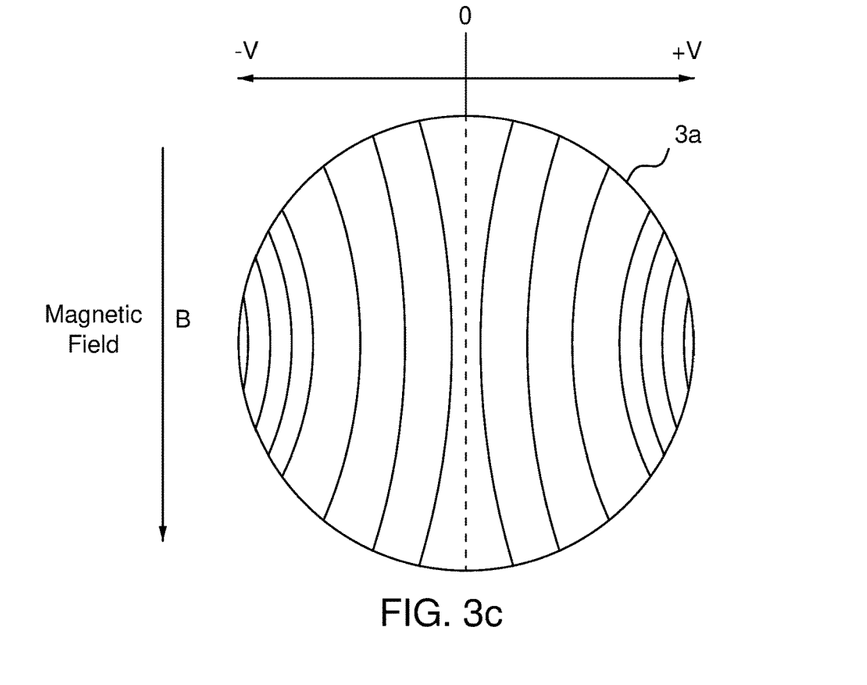

FIG. 3c illustrates the induced voltage created from the electrical current density in 3b.

Figure 3D:
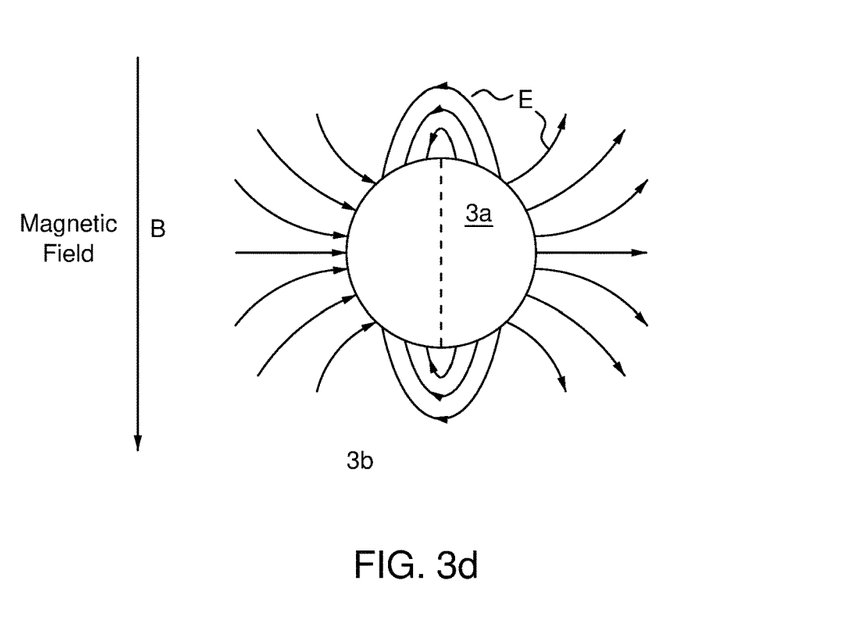

FIG. 3d illustrates the electrical field distribution created from the electrical potential in FIG. 3c in the nonconducting fluid phase 3b. Again, the denser lines represent increasing electric field strength.

Figure 3E:
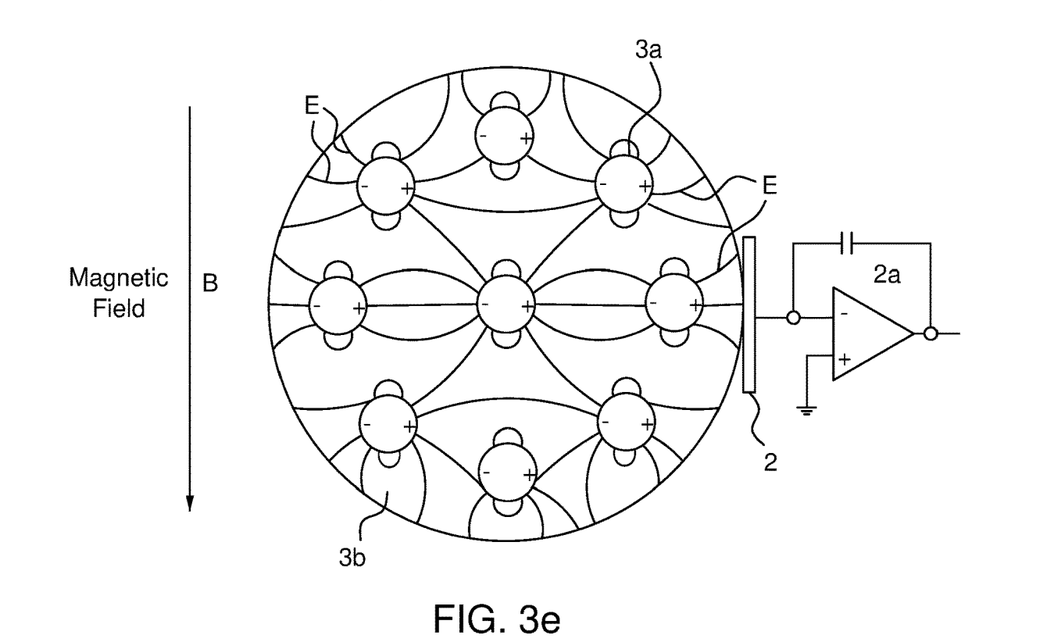

FIG. 3e illustrates the electrical field distribution E from multiple water droplets 3a traveling at a velocity in a non-conducting phase 3b. The electrical charge from these water droplets is capture by the electrode 2 and transfer to the low impedance circuit (charge amplifier) 2a. As discussed above the electrode 2 in this embodiment is positioned in a direction perpendicular to the magnetic field and flow to optimize the measurements, and the measured capacitance will provide a measure of the flow velocity.

Figure 4:
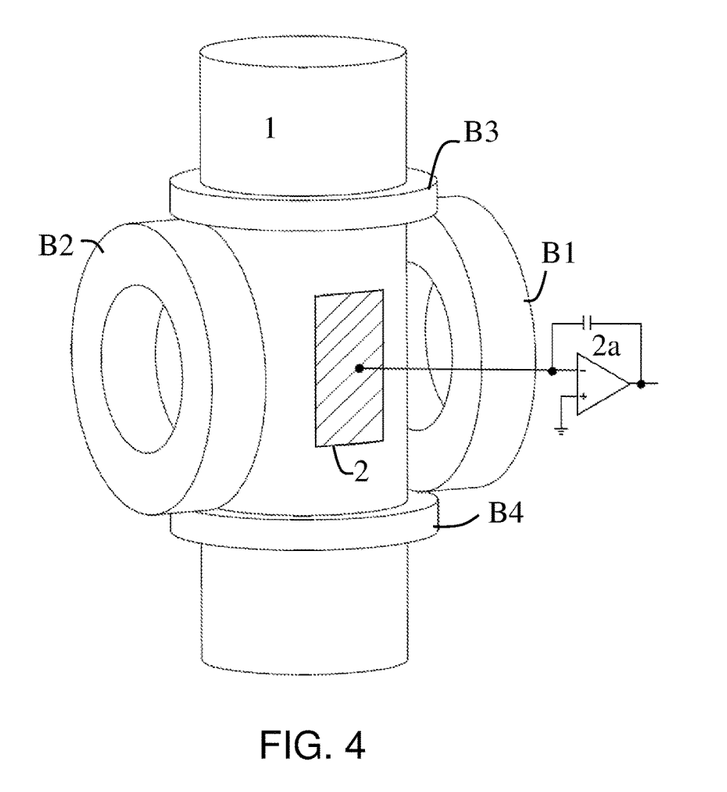
FIG. 4 illustrated the practical implementation of the present invention.

FIG. 4 illustrates a practical solution where the coils B1,B2 are positioned on opposite sides of the pipe 1. This may be combined with other measuring units, e.g. as disclosed above or in U.S. Pat. No. 7,276,916 B2 where they use additional coils B3,B4 for measuring Water Volume Fraction. It can also be combined with the solution discussed in WO2020084132/NO20181382, using the same electrodes but possibly with additional measuring circuits connected to them.

Figure 5:
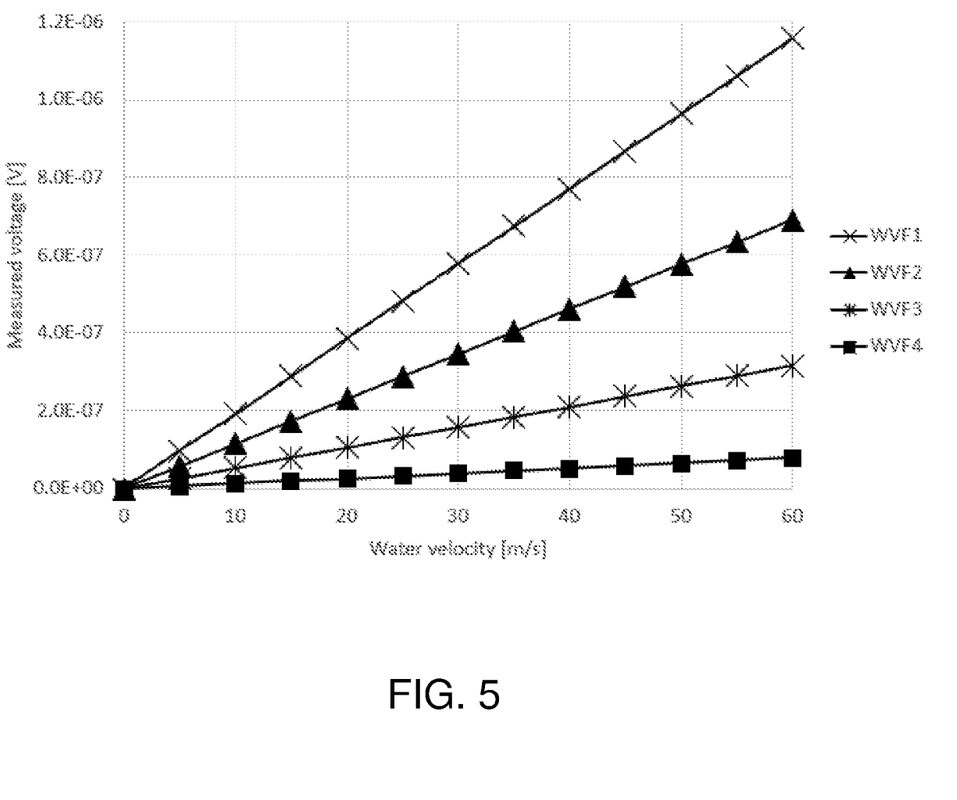
FIG. 5 illustrates the relationship between water velocity, WVF and voltage measured according to the present invention.

In FIG. 5 the output voltage from the charge measurement electronic 2a illustrated in FIG. 2b at different WVFs. The WVF1 is 40%, WVF2 is 20%, WVF3 is 10% and WVF4 is 5%. The graph demonstrates the relationship of the charge with water velocity and the WVF, and as can been seen the accuracy of the measurements is increased with the WVF, but depending on the sensor circuitry the measurements are reliable at least down to 5% WVF and less.

To summarize the present invention relates to a flow meter and corresponding method for measuring the flow velocity of an oil continuous multiphase flow where the flow includes water droplets, preferably having a known WVF. The meter includes at least one magnetic field generator configured to provide a magnetic field with a known strength into said flow and also at least one sensor for measuring the charge at the sensor relative to a ground level or reference level, the sensor may be a capacitance sensor or high impedance sensor. The sensor being positioned at a distance from the center of the magnetic field axis and the flow axis in essentially the same axial position as the magnetic field axis. The meter including calculating means for calculating a measure of the flow velocity based on the measured charge.

Preferably the at least one sensor is positioned at a distance in the perpendicular direction from the axis of the flow as well as the magnetic field in order to maximize the sensitivity of the measurements. In order to further increase the sensitivity at least two sensors may be positioned on opposite sides of the pipe and magnetic field. Another embodiment may include a plurality of sensors distributed along the inner pipe surface, the sensors being connected to a measuring instrument for by analyzing the charge distribution determining the velocity distribution over the flow cross section.

The magnetic field strength may be time varying magnetic field strength and the flow meter may then be configured to measure the response of the varying field on said at least one sensor.

The at least one sensor is positioned in the pipe wall and may be electrically insulated from the flow or be in electric contact with the flow depending on the available sensor and application.

The flow meter may also include a water volume fraction measuring instrument, measuring the water content of the flow, the calculation means being adapted to calculate the velocity also based on the determined water content or a storage device including predetermined information regarding the water content of the fluid flow, the calculation means being adapted to calculate the velocity also based on the determined water content. The calculation unit is calibrated based on a known flow conditions, measuring the velocity of the flow based on the measured deviations from the known flow conditions.

The invention claimed is:

1. A flow meter for measuring flow velocity of water in an oil continuous multiphase flow, the flow meter comprising:
at least one magnetic field generator configured to provide a magnetic field with a known strength into the oil continuous multiphase flow;
at least one sensor for measuring the charge at the sensor relative to a ground level, the sensor having low impedance circuitry and being positioned at a distance from the center of a magnetic field axis and a flow axis, in essentially the same axial position as the magnetic field axis;
wherein the flow meter is adapted to calculate a measure of the flow velocity based on the measured charge; and a water volume fraction measuring instrument, measuring water content of the oil continuous multiphase flow, the flow meter being adapted to calculate the water velocity also based on the determined water content.

2. The flow meter according to claim 1, wherein the at least one sensor is positioned at a distance in the perpendicular direction from the axis of the oil continuous multiphase flow as well as the magnetic field.

3. The flow meter according to claim 1, comprising at least two sensors positioned on opposite sides of a pipe and the magnetic field.

4. The flow meter according to claim 1, wherein the magnetic field has a time varying magnetic field strength, the flow meter being configured to measure a response of the varying field on the at least one sensor.

5. The flow meter according to claim 1, wherein the at least one sensor is positioned in a pipe wall electrically insulated from the oil continuous multiphase flow.

6. The flow meter according to claim 1, wherein the at least one sensor is positioned in a pipe wall in electrical contact with the oil continuous multiphase flow.

7. The flow meter according to claim 1, comprising a plurality of sensors distributed along the inner pipe surface, the sensors being connected to a measuring instrument for determining a water velocity distribution over a flow cross section.

8. A flow meter for measuring flow velocity of water in an oil continuous multiphase flow, the flow meter comprising:
    at least one magnetic field generator configured to provide a magnetic field with a known strength into the oil continuous multiphase flow;
    at least one sensor for measuring the charge at the sensor relative to a ground level, the sensor having low impedance circuitry and being positioned at a distance from the center of a magnetic field axis and a flow axis, in essentially the same axial position as the magnetic field axis;
    wherein the flow meter is adapted to calculate a measure of the flow velocity based on the measured charge; and
    a storage device including predetermined information including the water content of the oil continuous multiphase flow, the flow meter being adapted to calculate the water velocity also based on the predetermined water content.

9. A flow meter for measuring flow velocity of water in an oil continuous multiphase flow, the flow meter comprising:
    at least one magnetic field generator configured to provide a magnetic field with a known strength into the oil continuous multiphase flow;
    at least one sensor for measuring the charge at the sensor relative to a ground level, the sensor having low impedance circuitry and being positioned at a distance from the center of a magnetic field axis and a flow axis, in essentially the same axial position as the magnetic field axis;
    wherein the flow meter is adapted to calculate a measure of the flow velocity based on the measured charge; and
    wherein the calculation unit is calibrated based on known flow conditions, measuring the velocity of the water based on measured deviations from the known flow conditions.

10. A method for measuring the flow velocity of water in a hydrocarbon continuous fluid flow in a pipe of the fluid, the method comprising:
    applying a magnetic field across the hydrocarbon continuous fluid flow;
    using a sensor at a pipe wall positioned outside a magnetic field axis, measuring charge at the sensor, the sensor having low-impedance circuitry;
    calculating water flow velocity based on the measured charge at the sensor; and
    wherein the water flow velocity is calculated based on measured charge and water volume fraction ("WVF") of the hydrocarbon continuous flow.

11. The method according to claim 10, comprising measuring the WVF of the hydrocarbon continuous flow prior to the calculation.

* * * * *